United States Patent [19]

Collingwood et al.

[11] Patent Number: 4,603,226

[45] Date of Patent: Jul. 29, 1986

[54] PROCESS FOR MANUFACTURING CREOSOTE WITH NON-SETTLING OUT SALTS

[75] Inventors: George H. Collingwood, Sparta; Gail L. Erickson, Asbury, both of N.J.; Howard L. Simon; Roger L. Haley, both of Russell, Ky.; Bill E. Sparling, South Point, Ohio

[73] Assignee: Allied Corporation, Morris Township, N.J.

[21] Appl. No.: 801,455

[22] Filed: Nov. 25, 1985

[51] Int. Cl.$^4$ ............................................. C07C 39/02
[52] U.S. Cl. .................................... 568/716; 568/749
[58] Field of Search .................. 568/716, 749, 780

[56] References Cited

U.S. PATENT DOCUMENTS 1,025,616  5/1912  Elgerd ............................... 568/716

Primary Examiner—Werren B. Lone
Attorney, Agent, or Firm—Arthur J. Plantamura; Jay P. Friedenson

[57] ABSTRACT

A stable creosote product is prepared from which little or no sludge heel settles and which does not require heat to be applied to prevent settling out of solids. The stable product is obtained by a method that mechanically reduces the particle size or the salts that form upon cooling below the limpid point. The layer of salt which settles on the bottom of the beaker is then mechanically broken and homogenized. The fine salts which had previously settled and were homogenized, did not resettle but remained relatively evenly dispersed throughout the mixture and remained dispersed even after prolonged periods of uninterrupted standing. The salts are not allowed to settle before homogenizing. Little or no heel formation was detected in the creosote in which the settled and material was homogenized as described.

5 Claims, 1 Drawing Figure

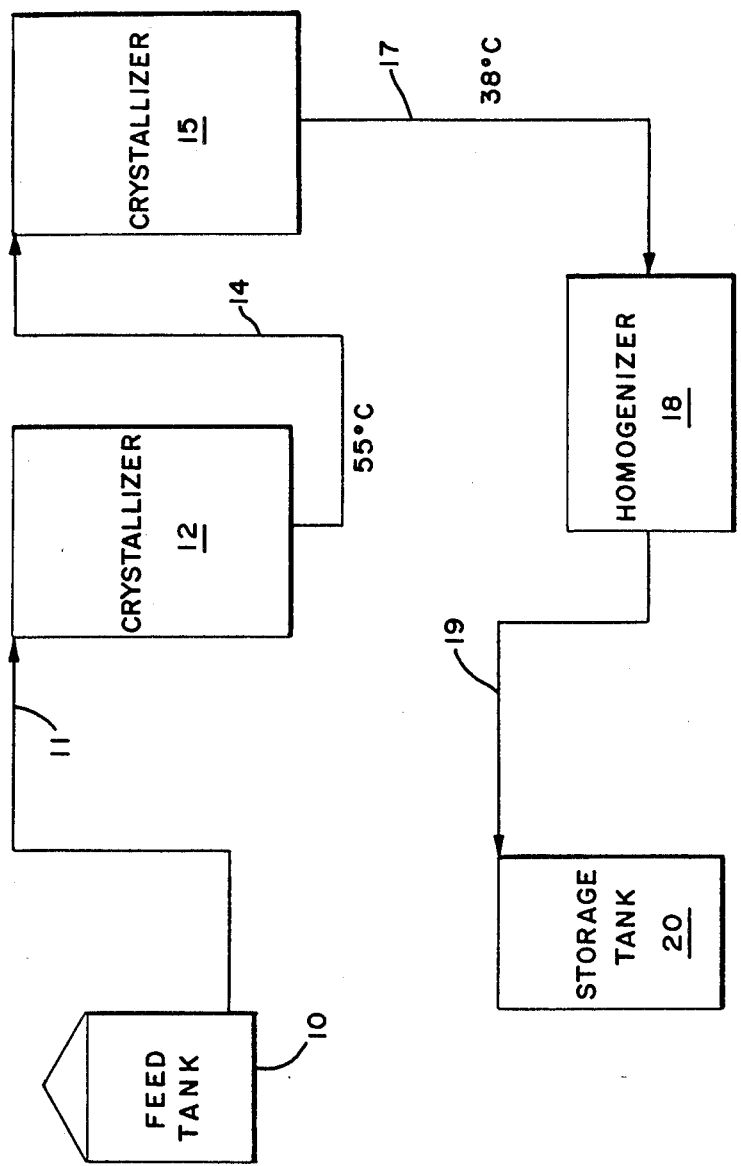

PROCESS FOR MANUFACTURING CREOSOTE WITH NON-SETTLING OUT SALTS

This invention relates to a method for making a stable creosote product. More particularly, the invention relates to the discovery of a method for the production of creosote products which has the advantageous property of being essentially free from the problems resulting from solids salting out from the product. The improved creosote prepared according to the invention also benefits from properties that permit it to be stored at ambient temperatures rather than at elevated temperatures thereby affording an energy savings advantage.

BACKGROUND OF THE INVENTION

At the present time, creosote is collected as a by-product during the distillation of coal tar to produce pitch. This creosote is a valuable by-product and is sold into the woodtreating industry as a perservative for treating wood to be used as railroad crossties, telephone poles, pilings, and many other end uses.

Creosote, as it is presently made, sold, and used, contains materials which will settle out as salts as the temperature decreases. Examples of these salt materials are, anthracene, phenanthrene, fluoranthene, and carbazole. The lower the temperature, and the longer the time that the creosote remains at lower temperatures, the more salts that form and settle. It is possible to remove most of these salts by cooling and filtering, but the market for such salts is limited and their value is such that the cost of recovery usually exceeds their worth. For this reason, the salts are normally left in the creosote oil. Additionally, it is felt by some that these materials add to the value of the creosote as a preservative; and therefore, should be retained in the creosote. In any case, these salts are seldom separated and recovered in the United States today, although in Europe, anthracene is still commercially recovered.

When these salts form and settle from the creosote, a sludge heel is formed which is difficult to put back into solution and also difficult to manage from a disposal aspect. Although it is possible to force the salt heel back into solution with sufficient expenditure of energy, perhaps aided by agitation, it is generally not cost effective to do so. Therefore, storage tanks of creosote are generally maintained at a temperature hot enough to prevent at least most of the salt formation. This temperature which inhibits salt formation is typically in the range of 180° F. to 200° F. (82°–93° C.) and is maintained by the supplier as well as by the customer for the most part. The energy required to maintain these temperatures to prevent this salting out is significant and represents a substantial portion of both the suppliers' and the customers' cost of operation. Even with the current practice of heating the tanks, sludge heels form over a period of time and these deposits must be periodically removed from the storage tanks. This cleaning of the tanks is generally done manually and is expensive due to the difficulty of removal. In addition, the sludge is classified environmentally as hazardous and it must be disposed of as hazardous waste. Such disposal is expensive.

In addition to the problem with slude heels in storage tanks, a similar problem occurs in railcars or barges when creosote is shipped via rail or water. Even though the creosote is loaded hot, the oil cools in transit and salt heels form. Upon receipt of the barges and railcars, the oil is heated, generally by steam or hot oil. Despite the expenditure of much energy, part of the heel usually remains in the barges and railcars after unloading. If the vessel is not cleaned after each trip, the heel quickly grows, thus reducing the effective volume of the vessel and thereby increasing the transportation cost per gallon of oil unloaded. It is thus apparent that a need exists for a creosote which is stable and does not settle out and which does not require its being maintained at an elevated temperature to preclude formation of sludge heels.

SUMMARY OF THE INVENTION

The objective of the present invention is to provide a creosote product in which a sludge salt heel, which normally occurs when solids settle from the creosote oil, is inhibited from forming or is at least minimal. This is accomplished by deliberately cooling the creosote oil to settle solids therein and by use of a suitable mechanical or other agitation treatment to reduce the particle size, i.e. comminute the particles and minimize the settling out of the salt crystals. By using this particle breaking procedure, we have discovered that the solid salts in the creosote oil do not resettle but remained substantially relatively evenly dispersed throughout the mixture. Moreover, the salts remained substantially dispersed even after several weeks of uninterrupted standing without the formation of the conventional resultant heel of a kind which is difficult, if not essentially impossible, to pump.

BRIEF DESCRIPTION OF THE DRAWING

In the drawing a flow diagram is shown illustrating a typical processing of the creosote oil to inhibit slude heel formation.

DESCRIPTION OF THE PREFERRED EMBODIMENT

In accordance with the invention the undesirable settling and caking of solids to form a sludge termed the "salt heel" in creosote is essentially eliminated or substantially diminished by cooling the creosote oil and reducing the particle size of the salts. While a homogeneous blend of the post treated creosote is preferred, advantageous results are obtained even when the blend is substantially, although not completely homogeneous. The salts in the post treated creosote remain dispersed even after several weeks of uninterrupted standing with little or no heel formation developing in the holding container.

In carrying out the process of our invention, the creosote oil to be stabilized is brought to a sufficiently high elevated temperature so that all "salts" with or without the aid of agitation are in solution, preferably to about 10° C. above the limpid point of the creosote oil. The oil is then cooled from this relatively elevated temperature above its limpid point to a temperature below 100° F. (38° C.). The "limpid point" of creosote oil, as the term is used herein, is the temperature at which crystals disappear when the oil is gradually heated from a lower temperature. The cooling rate employed in the process of the invention in preparation for the settling particles reduction treatment may employ any known suitable means that expeditiously results in the formation of crystals. The crystals which form and settle are essentially eliminated by a suitable agitation or blending action that effectively disperses the settled crystal/liquor mixture and converts it to a relatively homogeneous blend of finer particles or crystals in the oil.

Cresote oils which are adapted for treatment to inhibit salt settling according to the invention, to produce stable, fine crystal-containing oils, include the so-called light, medium and heavy creosote oils. The invention is particularly adapted for use in treating the heavier creosote oils resulting from carrying tar distillations to harder pitches, and which oils have a relatively higher percentages of components boiling at about 355° C. and higher and which tend to crystallize on cooling of the oil.

While the oils contemplated for treatment according to my invention are extremely complex and have widely varying characteristics, they may be defined generally as distillates of coal tar or coke oven tar or fractions or mixtures thereof having boiling ranges predominantly within the range between about 200° C. and about 400° C., and having specific gravities of between about 1.03 and about 1.14. Many of the light creosote oils distill completely within the range between about 200° C. and about 355° C. while others, such as the so-called medium and heavy oils, notably the creosote oils from hard pitch distillations, may contain up to 50% of components distilling at 355° C. and above.

Such creosote oils, upon cooling to temperatures between about 10° C. and about 60° C. precipitate between about 0.5% and about 20% by weight (dry basis) of "anthracene salts", i.e. crystals containing essentially anthracene, carbazole, phenanthrene and the like, and usually precipitate between about 10% and about 20% of such crystallizable compounds. The creosote oils which contain between about 10% and about 20% (dry basis) of anthracene salts crystallizable in the above temperature range are preferred. In general the quantity and chemical composition of crystalline material resulting from ordinary cooling of the oils are substantially the same, other conditions being equal.

The cooling of the creosote oil as noted above may be effected by any suitable means that will lower the temperature of the oil to about 90° F. (32° C.). This can be done in a crystallizer, by means of a heat exchanger, or via some other known practical method. Any of a variety of commercially available apparatus such as Model No. MS-18 Homogenizer supplied by Gaulin Company can be used to substantially reduce the particle size of the creosote crystal formation. Preferably, the reduction in particle size is effected so as to yield an average particle size of less than about 150 microns. Reproducible quality control of the treated creosote oil may be effected by any suitable means such that which measures the particle size at a controlled temperature. When the particle size of the precooled settled particle creosote has been reduced, we have discovered that the solid re-dispersed crystalline material remains dispersed and the conventional heel formation that normally forms from the settling out crystalline deposit, tends not to form. The cooled crystalline/liquor mixture of creosote oils remain stable, non-caking and substantially non-settling over prolonged periods. The fluidity of any solid material tending to settle is amply sufficient to insure stability during storage and shipment and pumping under normal industrial conditions. Except in relatively severe low temperatures, or when pumping of the product is sought to be expedited at lower temperature, the creosote which has been redispersed according to the invention may be readily pumped leaving no substantial sludge cake residue at relatively very low temperatures pumping may be facilitated by application of heat to the holding container.

The invention will be further described by the following specific examples. It should be understood, however, that although these examples may describe in detail certain preferred operating conditions of the invention, they are given primarily for purposes of illustration and the invention in its broader aspects is not limited thereto.

EXAMPLE I

Production of a creosote which can be stored at ambient temperatures without settling out of salts.

Procedure: The procedure for this run was to allow a standard creosote distillate, characterized as AWPA Grade P1, to cool to ambient temperature (25° C.) and to place it in a "Waring" blender set on the highest speed position. Another sample of the standard creosote distillate, characterized in the same way, was placed in a beaker and was not agitated in any way. The former sample was agitated for two (2) minutes, after which some frothing was noted. However, no settling of salts was noted in the agitated sample. The control sample contained $\frac{3}{4}''$ thick heel formation on the bottom of the beaker. The two samples were filtered through a 100 mesh (150 micron) screen and weighed to determine salt content. The analysis showed that the control sample contained 22.3% salts retained on the 100 mesh screen, while the agitated sample contained only 12.5% retained on the 100 mesh screes.

The results showed that the agitated sample contained smaller particles, as evidenced by the filtration test, than the control sample. Also, the agitated sample showed considerably less settling than the control sample, from visual inspection. The smaller particle size produced on oil having less tendnecy to settle out salt particles.

EXAMPLE II

The objective of this example was to determine if reheating of the agitated oil alters the effects of blending.

Procedure: Following the procedure of Example 1, the agitated oil from Example 1 was reheated to 65.5° C. (150° C.) and allowed to cool back down to ambient temperature (25° C.). A visual inspection was made of the reheated oil to determine settling effects. The reheated oil, after cooling back down to ambient temperature, appeared similar to the control sample. Appreciable salts were found to settle out.

The results show that when the particles are redissolved and then recrystallized, the character of the particle proeprties revert back substantially to those of the original oil.

EXAMPLE III

The objective of this Example III was to determine if other blending or mixing instruments would create the same type of particle size reduction on a creosote distillate as the "Waring" blender.

Procedure: This example began with testing of fresh creosote distillate, characterized as AWPA Grade P1, as follows:

| | |
|---|---|
| Specific gravity | 1.0922 37.8° C. (100° F.) |
| Water content | 0.3% |
| Limpid point | 51.7° C. (125° F.) |

-continued

| Brookfield viscosity | 6 centipoise | 60° C. |
| --- | --- | --- |
| | 16 centipoise | 37.8° C. |
| | 7 centipoise | 48.9° C. |
| | 24 centipoise | 26.7° C. |

Then three samples of this oil were cooled to 26.7° C. (80° F.). One sample was put in a "Waring" blender set at high speed, another was put in a laboratory mixer (manufactured by the Arthur H. Thomas Co.) equipped with agitation blades. The third sample was a control sample.

The sample put in the blender was agitated for 30 seconds and tested as follows:

| Specific gravity | 1.092 | 26° C. |
| --- | --- | --- |
| Viscosity | 31 centipoise | 26.7° C. |

The sample put in the lab mixer was agitated for 2 minutes set at 1600 rpm blade rotation. All three samples were allowed to settle for 2 days, at which time a visual inspection of salt settling was done. The sample agitated in the blender was free of salts on the bottom of the breaker. The sample mixed in the lab mixer evidenced substantial accumulated salts on the bottom of the beaker.

The results show that not all types of mixers or agitators will sufficiently break particles up to allow them to remain suspended and not settle.

EXAMPLE IV

The objective of this example was to determine the effect on salting out when creosote oil was agitated at an elevated temperature above the limpid point.

Procedure: The creosote distillate used in the previous example as the original or unagitated oil was heated to 65.6° C. and agitated at high speed in a "Waring" blender. The oil was then allowed to cool to ambient temperature overnight. Salts were found to have settled on the bottom of the beaker via visual inspection indicating that it is important that the oil be cooled sufficiently to allow salts to form before particle size can be effectively mechanically broken up or reduced so that settling out will be minimal.

EXAMPLE V

The objective of this example was to repeat Example III using still another mixer.

Procedure: Creosote distillate, characterized as AWPW Grade P1, was cooled to 26.7° C. (80° F.). One sample was agitated at high speed in a "Waring" blender for 30 seconds. A second sample was mixed with a Lightning mixer (Lightning Mixing Co. Model "F") for 2 minutes. A third sample was placed in a beaker and used as a control. The samples were allowed to settle overnight. The sample mixed with the Lightning mixer appeared similar to the control sample, while that agitated in the "Waring" blender was free of salt settling. This further confirms, as does Example III that certain types of mixing equipment do not produce shear force to reduce particle size sufficiently to inhibit salt settling.

EXAMPLE VI

The objective of this example was to determine that optimum temperature that oil must be cooled to in order that optimum, or minimum settling occurs.

Procedure: The procedure called for heating a standard creosote distillate to 65.6° C. (150° F.) to assure that all salts are in solution. The distillate was then apportioned into 4 different beakers and cooled to 4 different temperatures. The temperatures were 32.2° C. (90° F.), 37.8° C. (100° F.), 43.3° C. (110° F.), and 48.9° C. (120° F.). Each was held overnight at these temperatures. Each portion was then agitated with a "Waring" blender at high speed for 30 seconds and allowed to cool to ambient temperature (25° C.). In all four cases, although some salting was noted by visual inspection and optimum temperature could not be decisively determined in each case, the settling was substantially less than the non-agitated product.

EXAMPLE VII

The objective of this example was to test the usefulness of a homogenizer for sufficiently breaking up salt particles in a creosote distillate.

Procedure: A small lab hand homogenizer was used; the unit was purchased from Fisher Scientific (Catalog Number 11-504-200). It consisted of a mixing bowl, a plunger, and an orifice. The oil was placed in the bowl at 23.8° C. (75° F.) and the plunger was used to force the creosote through the adjustable orifice at high pressure. The liquid creostoe emerged in a completely homogeneous state with no evidence of salting or settling after overnight storage. The analysis consisted of passing the oil through a 200 mesh screen;

Starting Material=21.2% salts retained

"Homogenized" Creosote=0.3% salts retained

The homogenized sample was then placed in a refrigerator overnight at 2.2° C. with no additional salting noted.

It was clear that the homogenizer did a satisfactory job in mechanically breaking the salt particles below 200 mesh (75)). It was also evident that this resulted in less settling and less additional salting even at low temperatures and overnight storage.

EXAMPLE VIII

The objective of this example was to observe size reduction equipment.

Procedure: The procedure consisted of using Gaulin Corporation's of Everett, Mass., Lab scale homogenizer. This machine pumps material through a valve assembly at high pressure and low velocity on the inlet side and with low pressure and high velocity on the exit side. This action creates a vapor pressure change causing the material to implode and thus break large particles into smaller ones. Creosote oil preheated above and then cooled below the limpid temperature as above described in Example 1. The results follow:

| Sample | Process | Outlet Temperature | Outlet % Salts |
| --- | --- | --- | --- |
| 1 | Original Oil | — | 7.1 |
| 2 | Homog. @ 3000 psi | 96° F. | 0.56/2.3 |
| 3 | Homog. @ 5000 psi | 104° F. | 1.2/1.1 |
| 4 | Homog. @ 8000 psi | 118° F. | 7.2/5.9 |

This homogenizer appeared to show the greatest potential for reducing particle size. The best homogenizing pressure appeared to be 3000 psig or 5000 psig.

EXAMPLE IX

Objective: The objective of this example was to observe long-term settling effects of creosote oil that had been homogenized.

Procedure: The procedure consisted of obtaining a 1 gallon can of creosote solution, heating it to 185° F. (85° C.) and then cooling it to 110° F. (43° C.). 1 quart of the creosote was homogenized using the smallest orifice opening. 1 quart of the original oil was set aside as a control sample. After 1 hour salts were felt with a stirring rod in the original oil, but not in the homogenized samples. 48 hours later, the original oil had 10.4% salts retained on a 200 mesh screen. 14 days later, no salts could be felt on the homogenized sample. However, particles were noted clinging to the stirring rod. The homogenized samples do not settle even after long periods of time.

EXAMPLE X

In this Example, rail car quantities of creosote homogenized according to the invention as in Example VIII (Car B) and creosote prepared in the conventional manner (Car A) were compared in their handling at a customer facility in Indianapolis, Ind. An attempt was made to pump the non-homogenized creosote (Car A) first, with no success. An attempt was made to pump the homogenized oil and no difficulties were experienced. The rail care (Car B) pumped empty in approximately 1 hour. There were virtually no solids left in the rail car (Car B). On two separate occasions, pumping of Car B had to be stopped for 10–15 minutes each, and restarted. No troubles were encountered. This was regarded as unusual since steam is ordinarily required to restart the lines once pumping stops in order to restart the pump.

An attempt to pump the non-homogenized oil (Car A) was then made by initiating flow with steam. Steam was blown into the bottom of the rail car for approximately ½ hour. Underneath the rail car the outlet valve, which was found to be clogged, was opened and steam was blown into the car for 10 more minutes. Pumping was then started. The rail car required about 1 hour and 15 minutes to unload and 7" of solids still remained in the bottom of the rail car.

Illustrated in the drawing is a flow diagram depicting generally the manner in which the non-salting creosote oil of the invention may be prepared where a continuous operation is employed. As shown, creosote oil which is above the limpid point from storage tank 10 is fed via line 11 to one or more crystallizers, 12 and 15, connected by line 14 in series. The crystallizers cool the oil to about 35° C. whereupon the salts come out of solution. The crystallizers are equipped with agitators to keep the salts suspended. The oil/salt slurry is then pumped through line 17 to a homogenizer 18 where for the purpose of reducing the average particle size to less than about 150 microns (AVE). From the homogenizer, the creosote goes through line 19 to a storage tank 20, or shipping container (not shown).

It will be understood that a great variety of products may be made within the ranges disclosed herein and therefore do not intend to limit the invention except as set forth in the claims which follow.

What is claimed is:

1. A process for producing a creosote oil which is stable against settling of salts which comprises:
   a. heating a coal tar distillate creosote oil to a temperature above its limpid point;
   b. allowing the creosote oil to cool to ambient temperatures of at least below 35° C. for the solid contents therein to come out of solution and form cyrstals; and
   c. disintegrating the salts formed in step a by mechanically breaking down the crystals until the crystal size of the resulting solid material has been substantially diminished and thereby redispersing the solid comprising the salts into the creosote liquid until a substantially uniform liquid dispersion is attained.

2. The process of claim 1 wherein the redispersed creosote oil average particle size is less than about 150 microns.

3. The process of claim 1 wherein the creosote oil in step a is heated to a temperature at least 10° C. above its limpid point.

4. The process of claim 1 wherein the creosote oil in step b was cooled to a temperature of between 0° C. and 40° C.

5. The creosote oil product obtained by the method of claim 1.

* * * * *